(12) United States Patent
Christoudias

(10) Patent No.: US 7,731,716 B1
(45) Date of Patent: Jun. 8, 2010

(54) IRRIGATION SET ADAPTOR AND CONTROL PANEL FOR ELECTRO-COAGULATION

(75) Inventor: George Christoudias, Teaneck, NJ (US)

(73) Assignee: Surgical Inventors & Innovations, Teaneck, NJ (US)

( * ) Notice: Subject to any disclaimer, the term of this patent is extended or adjusted under 35 U.S.C. 154(b) by 692 days.

(21) Appl. No.: 11/554,358

(22) Filed: Oct. 30, 2006

Related U.S. Application Data

(63) Continuation-in-part of application No. 11/277,803, filed on Mar. 29, 2006, now abandoned.

(51) Int. Cl.
*A61B 18/14* (2006.01)
(52) U.S. Cl. .......................................... 606/49; 606/42
(58) Field of Classification Search .................. 606/42, 606/45, 49
See application file for complete search history.

(56) References Cited

U.S. PATENT DOCUMENTS

| | | | | |
|---|---|---|---|---|
| 5,348,555 A | * | 9/1994 | Zinnanti | 606/49 |
| 5,514,089 A | * | 5/1996 | Walbrink et al. | 604/33 |
| 5,609,573 A | * | 3/1997 | Sandock | 604/22 |
| 5,662,647 A | * | 9/1997 | Crow et al. | 606/41 |
| 5,817,121 A | * | 10/1998 | Christoudias | 606/190 |
| 6,193,672 B1 | * | 2/2001 | Clement | 600/565 |
| 6,391,040 B1 | * | 5/2002 | Christoudias | 606/162 |
| 6,620,161 B2 | * | 9/2003 | Schulze et al. | 606/51 |
| 6,908,463 B2 | * | 6/2005 | Treat et al. | 606/29 |

\* cited by examiner

*Primary Examiner*—Lee S Cohen
(74) *Attorney, Agent, or Firm*—Richard A Joel, Esq.

(57) ABSTRACT

An adaptor for an irrigation set which includes an elongated cannula having an enlarged portion opposite the operative end thereof and a downwardly extending channel removably coupled to the manifold of a standard or label suction irrigation set for suction and irrigation fluids. The manifold is connected to suction and irrigation lines through respective valves. A bracket extends downwardly from the enlarged cannula portion and a hand control panel is mounted thereon with switches to activate cutting and electrocoagulation with an electrode, which is retractable within the cannula.

4 Claims, 2 Drawing Sheets

IRRIGATION SET ADAPTOR AND CONTROL PANEL FOR ELECTRO-COAGULATION

CROSS REFERENCE TO RELATED APPLICATIONS

This is a continuation in part application of Ser. No. 11/277,830 filed on Mar. 29, 2006, now abandoned.

STATEMENT REGARDING FEDERALLY SPONSORED RESEARCH OR DEVELOPMENT

Not Applicable

PARTIES TO A JOINT RESEARCH AGREEMENT

Not Applicable

BACKGROUND OF THE INVENTION

This invention comprises a new and improved instrument for irrigating and dissecting tissue during laparoscopic procedures and is a continuation-in-part of applicant's co-pending application Ser. No. 11/277,803, filed Mar. 29, 2006.

DESCRIPTION OF RELATED ART INCLUDING INFORMATION DISCLOSED UNDER 37 CFR 1.97 & 1.98

U.S. Pat. No. 6,620,161 to Schulze et al discloses an electrosurgical instrument useful in controlling-coagulating blood vessels such as veins and arteries. The instrument includes a handle assembly with first and second actuators and an elongated tube assembly, which is supplied with current for grasping and dissecting tissue.

U.S. Pat. No. 6,908,463 to Treat et al discloses an electrothermal device for sealing and dividing tissue, which is particularly suitable for laparoscopic and endoscopic surgery.

The prior art, however, fails to disclose the unique instrument adaptor of the present invention which is simple to use, highly manipulative and inexpensive. The adaptor may be used with numerous commercially available endodissectors. The electrode for dissecting is retractable within a lumen, which also includes concentric space about the electrode for irrigation and suction or alternatively, the electrode could be easily withdrawn within the lumen to facilitate irrigation and suction. A detachable control panel on the handle regulates the current at the tip for either coagulation or cutting. A pair of switches mounted on the handle for the lumen and electrode controls a pair of tube lines coupled to a manifold for irrigation or suction during a procedure. Advantageously, dissecting, irrigation and suction may be performed with a single handheld instrument. Electrocoagulation is operated in conjunction with an electrodissecting design having a gauze dissector tip. A suction-irrigation system is coupled thereto on the same instrument for one-handed operation.

BRIEF SUMMARY OF THE INVENTION

This invention involves a unique adaptor that will allow the cannula with the endodissector, the retractable electrode, and the detachable electrocautery control panel, to be used with any irrigation set thus empowering any irrigation set to perform blunt dissection, irrigation, aspiration, electrocoagulation and simultaneous smoke exhaustion. This eliminates the need for instrument exchanges when these functions are performed.

The lumen is connected to a manifold at the non-working end, which has an inlet on one side thereof, an outlet on the other side; and is mounted on a handle to manipulate the dissector. An inlet tube is connected to the lumen for irrigation purposes, whereas the other outlet tube is connected to the lumen for suction purposes. Respective plungers are mounted to the manifold to control the flow that can be adjusted at variable volumes from the inlet tubing and the outlet tubing. The tubing is connected to the respective manifold openings. The color-coded trigger-like plunger valves open or close the respective tubing as desired or alter the flow at different volumes.

This invention involves a unique adaptor for use in laparoscopic surgery, which combines an irrigation set for suction and irrigation with an electrode for cutting and electro-coagulation. A pistol grip manifold is coupled to separate suction and irrigation lines through trigger valves. The manifold is connected to a transversely mounted adaptor, which leads to an elongated cannula or lumen. The cannula has an opening at its rear end for insertion of an electrode which protrudes from the front end of the cannula to engage tissue, etc. A control panel is removably mounted on a bracket extending downwardly from the adaptor to above the triggers. The panel permits activation of the electrode for cutting or coagulation. The cannula has means for attachment to a gauze dissector with a lumen at the front end for dissection or retraction of tissue. With the same hand, the triggers can be operated for irrigation of the wound and suction of the fluid from the wound site or for blunt dissection and/or retraction of tissues.

Accordingly, an object of this invention is to provide a new and improved adaptor for use of the multifunctional cannula with any irrigation set.

Another object of this invention is to provide a new and improved device with a trigger grip for irrigation and suction coupled to an adaptor, which is connected to an elongated cannula, and has a control panel for an electrode mounted to the adaptor.

Another object of this invention is to provide a new and improved irrigation system and endodissector for one hand operation, which includes a dissecting electrode mounted within an elongated lumen, which is also used for irrigation and suction with the controls for these activities resting within the reach of the activating digit i.e., the thumb.

A more specific object of this invention is to provide a new and improved device having an elongated cannula coupled with an adaptor to a pistol grip suction and irrigation arrangement and having a control panel for a cutting and coagulation electrode extending downwardly from an adaptor on the cannula to permit one hand operation of the device.

A further object of this invention is to provide a new and improved blunt dissector, which includes an electrode slidable within a lumen and an adaptor mounted to a manifold with separate lines under control of respective valves connected to said manifold for purposes of irrigation and suction in a single instrument.

Another object of this invention is to provide a new and improved dissector adaptor for any irrigation set, which includes control means located on a manifold to regulate the irrigation and suction action of the lumen as desired during a dissecting procedure and a switch conveniently and detachably mounted to the lumen to control current for dissecting and coagulation with a unique slim tip electrode.

BRIEF DESCRIPTION OF THE DRAWINGS

The above and other objects and advantages of the present invention may be more clearly seen when viewed in conjunction with the accompanying drawings wherein:

The above and other objects and advantages of the present invention may be more clearly seen when viewed in conjunction with the accompanying drawings wherein:

FIG. 2a is a side view of a 5 mm cannula while

DETAILED DESCRIPTION OF THE INVENTION

Figure 1:
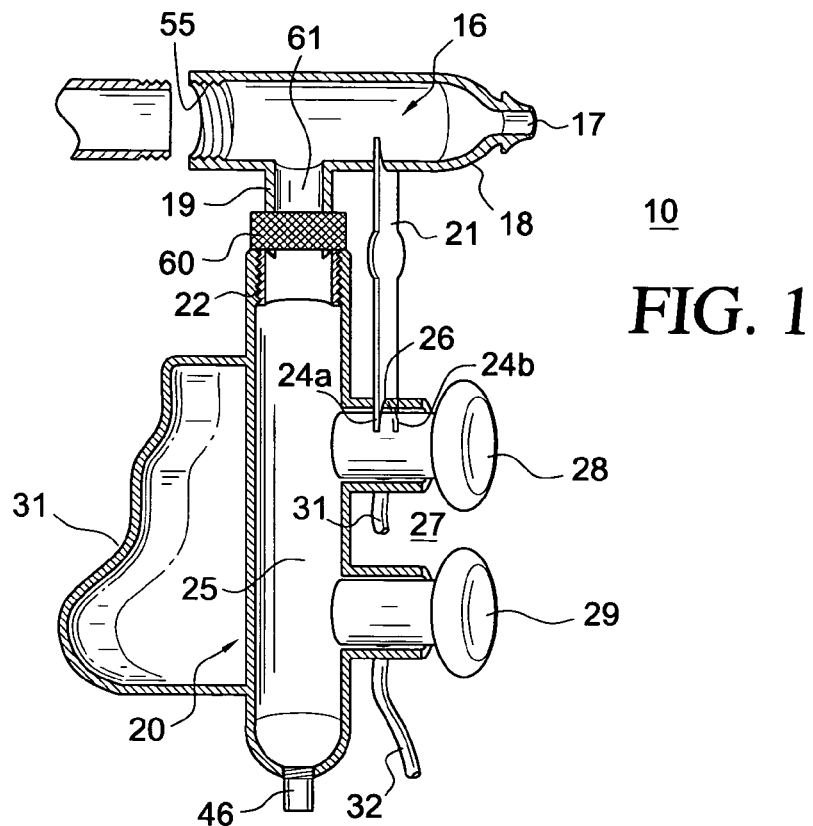
FIG. 1 is a perspective view of the irrigation set and control panel.
Figure 2A:
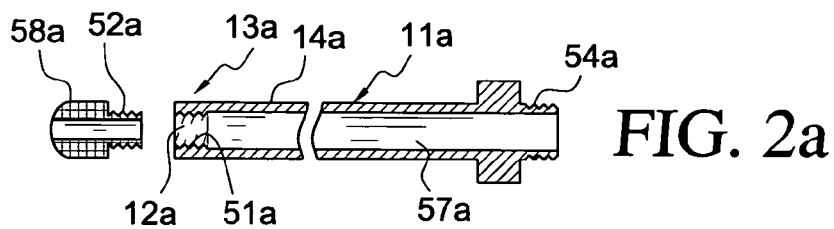
Figure 2B:
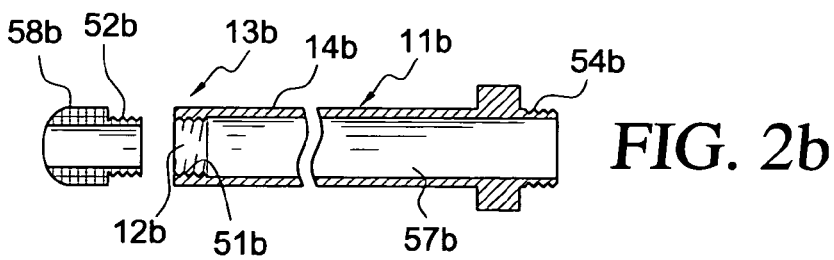
FIG. 2b is a side view of a 10 mm cannula.
Figure 3A:
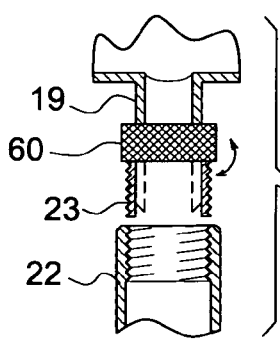
FIG. 3a is a cross-sectional view of the adaptor attached to the cannula and FIG. 3b is a cross-sectional view of the adaptor secured to the manifold for the suction and irrigation lines.
Figure 3B:
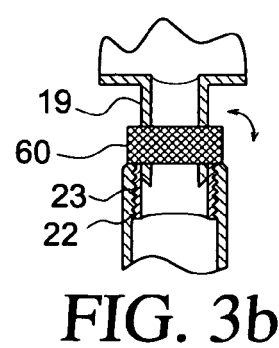
Figure 4:
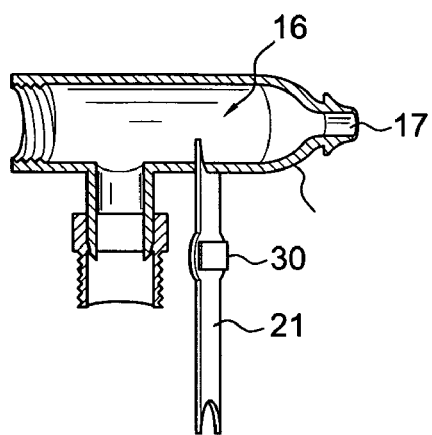
FIG. 4 is a cross-sectional view of the cannula and the downwardly extending adaptor coupling and support member.

Referring to FIGS. 1, 2a and 2b of the drawings, the instrument 10 of this invention comprises an elongated cannula 11a or 11b having an aperture 12a or 12b at the operative end 13a or 13b an intermediate elongated cylindrical body 14a or 14b, mounted to an enlarged adaptor 16 having an aperture 17 at the end 18.

The 10 mm cannula 11b or the 5 mm cannula 11a include threaded portions 54b and 54a respectively which engage the internal threads 55 on the adaptor 16. An elongated slim tip electrode (not shown) is inserted into aperture 17 and extends along the central opening 57a or 57b of the cannula through the dissector 58a or 58b and projects outwardly therefrom to engage tissue for cutting or coagulation purposes.

The enlarged adaptor 16 includes a downwardly extending tubular portion 19 and a flat plate portion 21 also extending downwardly adjacent the end 18. The tubular portion 19 includes an exteriorly threaded end portion 23 mounted thereabout which nests in the cylindrical aperture 22 in the plastic pistol grip handle 20. The threaded coupling 23 with a knurled gripping portion 60 which extends outwardly and secures the cannula 11 to the handle 20 by engaging the internally threaded aperture 22.

The flat portion 21 includes outwardly flaring sides 24a, 24b with a curved cutout lower portion 26, which engages the exterior of the plunger section 27.

The aperture 61 is located in the upper portion of a manifold 25, which includes plungers 28 and 29 coupled thereto. The plungers 28 and 29 are coupled respectively to an inlet hose 31 and a suction hose 32. When the plunger 28 or 29 is pushed a flow path is opened to the manifold 25 for suction or irrigation purposes. The plungers 28 and 29 are color coded for ease of recognition and use. The manifold 25 also includes a lower threaded plug 46 for cleanout purposes and a shaped axial support 31 to engage one's palm.

Figure 6:
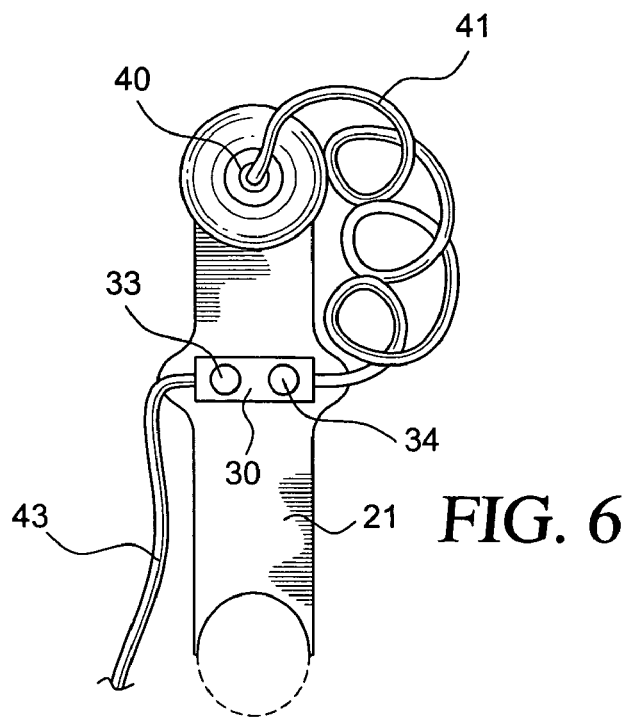
FIG. 6 is a schematic view of the control panel mounted on the support member and coupled to an electrode; and, FIG. 7 is a schematic view of the electrode coupled to the control panel for electro-coagulation.
Figure 5:
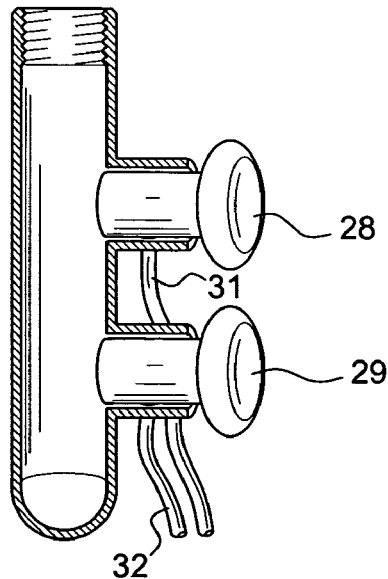
FIG. 5 is a view of the manifold and plunger valves which connects to the adaptor coupling of FIG. 4.
Figure 7:
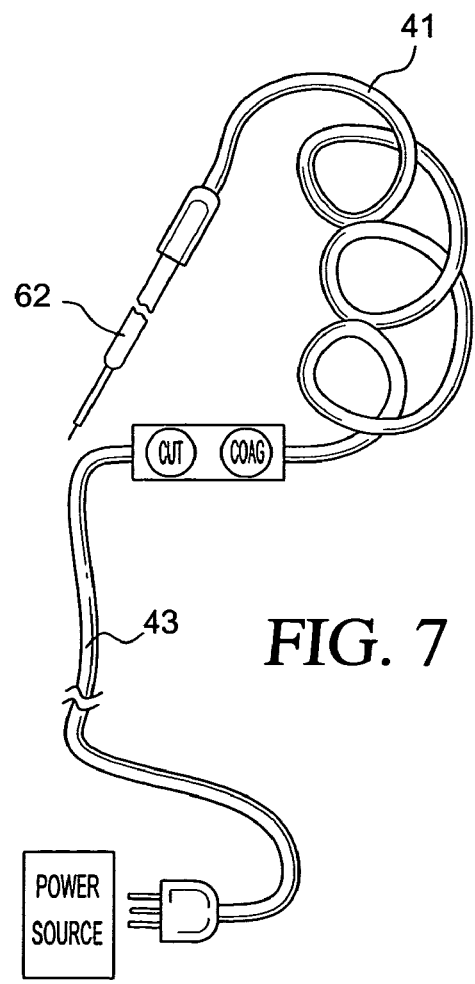

The flat portion 21 includes a control panel 30 removably mounted thereto. A typical control panel 30 shown in FIGS. 6 and 7 includes coagulation switch 33 and a cutting switch 34 depending on the desired operation with the electrode 40. The electrode 40 is inserted through the aperture 17 and extends outwardly from the aperture 12a and 12b at the operational end 13. The control panel 30 is coupled to the electrode 40 by the coiled wire 41 and to a power source 42 by wire 43.

To operate, the instrument 10 and specifically the cannula 11 is inserted into a body port and the electrode 40 with a particular slim tip electrode 62 is extended to contact the particular tissue. The switches 33 and 34 on the control panel 30 control the current to the electrode 40. The cutting switch 34 is activated for dissection and then the coagulation switch 33 is activated. The plungers 28 and 29 are then sequentially operated for irrigation and suction of the site. The operations are all conveniently performed with the same handheld instrument with a particular digit such as a thumb.

Each adaptor 16 is specifically made for each and every brand or generic irrigation set to allow secure fitting of the suction irrigation cannula 11a or 11b with a gauze endodissector. The adaptor includes a retractable electrode 40 and a detachable control panel 30 on the irrigation-suction set. Without adaptor 16, many commercially available irrigation sets cannot perform all of the functions described above in a single instrument.

While the invention has been explained by a detailed description of certain specific embodiments, it is understood that various modifications and substitutions can be made in any of them within the scope of the appended claims that are intended also to include equivalents of such embodiments.

What is claimed is:

1. An irrigation set adaptor for electrocoagulation with any suction irrigation set comprises:
    a multifunctional cannula having an elongated body including a channel extending therealong having an operative channel aperture at one end and a second channel aperture at the opposite end;
    an enlarged adaptor mounted to the second channel aperture and having a downwardly extending threaded cylindrical portion;
    a manifold coupled to the threaded cylindrical portion of the adaptor;
    a first irrigation tube and a second suction tube coupled to the manifold at one end of each tube;
    an irrigation valve and a suction valve connected to the respective tubes to regulate the manifold flow and means for providing fluid to the irrigation tube and means for receiving fluid from the suction tube through the respective valves;
    an electrode having a cutting end and a connecting end, said electrode being slidably mounted within the cannula channel and extending outwardly at the cutting end and at the opposite connecting end of said electrode, said irrigation set adaptor further including;
    a power supply;
    a control panel coupled to the connecting end of the electrode at one end and to the power supply at the other end;
    means for securing the adaptor comprising threaded manifold means for meshing with the threaded cylindrical portion of the adaptor; and,
    wherein the control panel regulates the current to the electrode for cutting or alternatively for coagulation and wherein the suction tube may be operated simultaneously with the electrode.

2. An irrigation set adaptor in accordance with claim 1 wherein:
    the cylindrical portion includes an externally threaded portion, an internally threaded member engaging said threaded portion and having a downwardly externally extending thread portion and the manifold includes an upper internally threaded aperture to be engaged by the threaded member joining the manifold to the adaptor.

3. An irrigation set adaptor in accordance with claim 2 wherein:

the threaded member includes an enlarged hollow gripping portion at its upper end and a cylindrical threaded portion extending downwardly therefrom and the downwardly extending portion of the adaptor includes a lower end which engages and stops the movement of the threaded cylindrical portion.

4. An irrigation set adaptor in accordance with claim 3 wherein:

the enlarged adaptor includes a bracket extending downwardly therefrom having a control panel detachably mounted thereto.

\* \* \* \* \*